United States Patent
Muraki et al.

(10) Patent No.: US 9,857,286 B2
(45) Date of Patent: Jan. 2, 2018

(54) PARTICLE FRACTIONATION APPARATUS, PARTICLE FRACTIONATION METHOD AND PARTICLE FRACTIONATION PROGRAM

(71) Applicant: Sony Corporation, Tokyo (JP)

(72) Inventors: Yosuke Muraki, Tokyo (JP); Atsuo Fujimaki, Tokyo (JP); Fumitaka Otsuka, Tokyo (JP); Yasunobu Kato, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/028,411

(22) PCT Filed: Oct. 10, 2014

(86) PCT No.: PCT/JP2014/005167
§ 371 (c)(1),
(2) Date: Apr. 8, 2016

(87) PCT Pub. No.: WO2015/056431
PCT Pub. Date: Apr. 23, 2015

(65) Prior Publication Data
US 2016/0245736 A1    Aug. 25, 2016

(30) Foreign Application Priority Data
Oct. 17, 2013  (JP) .................................. 2013-216633

(51) Int. Cl.
*B07C 5/02*    (2006.01)
*G01N 15/14*   (2006.01)
(Continued)

(52) U.S. Cl.
CPC ......... *G01N 15/1425* (2013.01); *B03C 7/003* (2013.01); *G01N 15/14* (2013.01);
(Continued)

(58) Field of Classification Search
CPC ..... G01N 2015/149; G01N 2015/0065; G01N 2015/1081; B03C 7/003
(Continued)

(56) References Cited

U.S. PATENT DOCUMENTS 3,710,933 A    1/1973    Fulwyler et al.
3,924,947 A    12/1975   Hogg
(Continued)

FOREIGN PATENT DOCUMENTS

GB    1 103 190 A    2/1968
JP    2006-292769 A    10/2006
(Continued)

OTHER PUBLICATIONS

Yoshimura et al., The Latest Technology [Modern Technology] of a Cell Sorter, Applied Research Report, Jasco Report. 1990;32(1):1-20.
(Continued)

*Primary Examiner* — Terrell Matthews
(74) *Attorney, Agent, or Firm* — Wolf, Greenfield & Sacks, P.C.

(57) ABSTRACT

A particle fractionating apparatus is described that can sort droplets containing particles in a first mode of operation, and distribute droplets that do not contain particles to a plurality of locations in a second mode of operation. The modes of operation are selectable by a user. Droplets may be emitted from a microchip of the particle fractionating apparatus.

19 Claims, 2 Drawing Sheets

(51) Int. Cl.
*B03C 7/00* (2006.01)
*G01N 15/00* (2006.01)
*G01N 15/10* (2006.01)

(52) U.S. Cl.
CPC ............... *G01N 2015/0065* (2013.01); *G01N 2015/1081* (2013.01); *G01N 2015/149* (2013.01)

(58) Field of Classification Search
USPC ............... 209/3.1, 3.2; 250/564, 574, 461.2; 356/336
See application file for complete search history.

(56) References Cited

U.S. PATENT DOCUMENTS

| | | | | |
|---|---|---|---|---|
| 4,173,415 | A | * | 11/1979 | Wyatt ............... G01N 15/1459 250/564 |
| 4,284,496 | A | | 8/1981 | Newton |
| 4,318,480 | A | * | 3/1982 | Lombardo ......... G01N 15/1404 209/3.1 |
| 4,318,481 | A | * | 3/1982 | Lombardo ......... G01N 15/1404 209/3.1 |
| 4,538,733 | A | * | 9/1985 | Hoffman ................ B07C 5/36 209/3.1 |
| 5,180,065 | A | * | 1/1993 | Touge ................ G01N 15/1404 209/3.1 |
| 5,776,781 | A | * | 7/1998 | Vardanega ................ B01L 1/04 209/3.1 |
| 6,248,590 | B1 | | 6/2001 | Malachowski |
| 6,949,715 | B2 | | 9/2005 | Kelly |
| 7,019,293 | B1 | * | 3/2006 | Hamada ................ G01B 15/00 250/310 |
| 7,417,734 | B2 | | 8/2008 | Kanda |
| 7,758,811 | B2 | * | 7/2010 | Durack ................ C12N 5/0612 422/67 |
| 8,570,511 | B2 | * | 10/2013 | Wang ................ G01N 15/0266 356/335 |
| 9,029,724 | B2 | * | 5/2015 | Hashimoto ............ G01N 15/14 209/128 |
| 9,087,371 | B2 | | 7/2015 | Muraki |
| 9,339,823 | B2 | | 5/2016 | Muraki et al. |
| 2008/0092655 | A1 | | 4/2008 | Takiguchi |
| 2011/0081684 | A1 | | 4/2011 | Gauer et al. |
| 2011/0284378 | A1 | * | 11/2011 | Shinoda ................ B01L 3/0268 204/603 |
| 2013/0256136 | A1 | | 10/2013 | Muraki et al. |
| 2013/0258075 | A1 | | 10/2013 | Muraki et al. |
| 2014/0087453 | A1 | | 3/2014 | Tahara |
| 2014/0144817 | A1 | | 5/2014 | Hashimoto et al. |
| 2014/0193059 | A1 | | 7/2014 | Muraki |
| 2015/0057787 | A1 | | 2/2015 | Muraki et al. |
| 2015/0068957 | A1 | | 3/2015 | Otsuka et al. |
| 2015/0204774 | A1 | | 7/2015 | Ito |
| 2015/0285726 | A1 | | 10/2015 | Tanase et al. |
| 2015/0285727 | A1 | | 10/2015 | Muraki |
| 2016/0223451 | A1 | | 8/2016 | Muraki et al. |
| 2016/0266027 | A1 | | 9/2016 | Muraki et al. |

FOREIGN PATENT DOCUMENTS

| | | |
|---|---|---|
| JP | 2007-532874 A | 11/2007 |
| JP | 2008-107110 A | 5/2008 |
| JP | 2009-198511 A | 9/2009 |
| JP | 2010-510782 A | 4/2010 |
| JP | 2010-190680 A | 9/2010 |

OTHER PUBLICATIONS

Bonner et al., Flourescence Activated Cell Sorting. Review of Scientific Instruments. Mar. 1972; 43(3):404-9.
U.S. Appl. No. 13/788,075, filed Mar. 7, 2013, Muraki et al.
U.S. Appl. No. 13/788,165, filed Mar. 7, 2013, Muraki et al.
U.S. Appl. No. 14/026,023, filed Sep. 13, 2013, Tahara.
U.S. Appl. No. 14/118,788, filed Nov. 19, 2013, Muraki.
U.S. Appl. No. 14/118,994, filed Nov. 20, 2013, Hashimoto et al.
U.S. Appl. No. 14/386,368, filed Sep. 19, 2014, Otsuka et al.
U.S. Appl. No. 14/386,499, filed Sep. 19, 2014, Muraki et al.
U.S. Appl. No. 14/413,543, filed Jan. 8, 2015, Ito.
U.S. Appl. No. 14/440,765, filed May 5, 2015, Tanase et al.
U.S. Appl. No. 14/737,370, filed Jun. 11, 2015, Muraki.
U.S. Appl. No. 15/028,419, filed Apr. 8, 2016, Muraki et al.
U.S. Appl. No. 15/093,879, filed Apr. 8, 2016, Muraki et al.

\* cited by examiner

[Fig. 1]
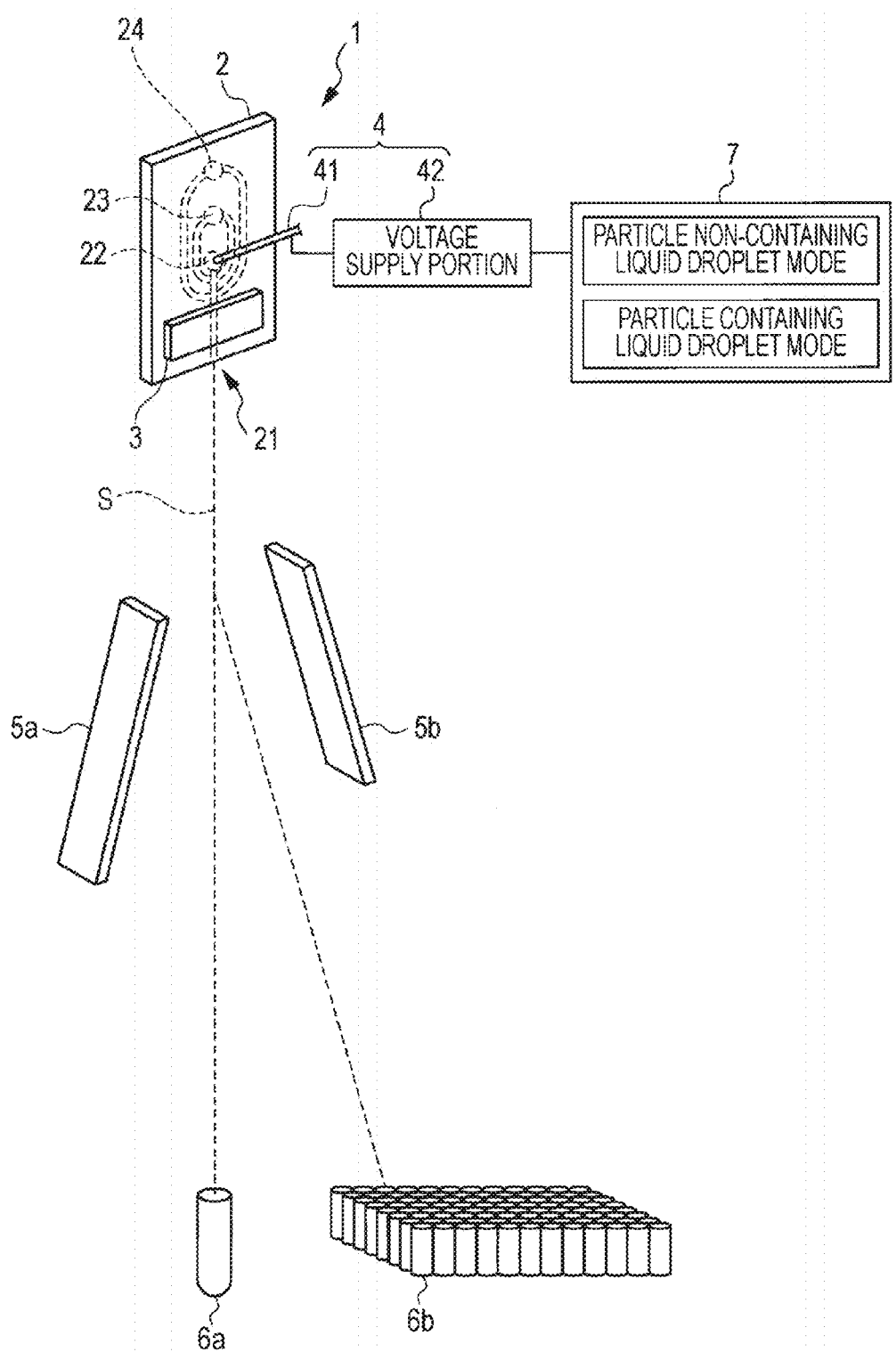

[Fig. 2]
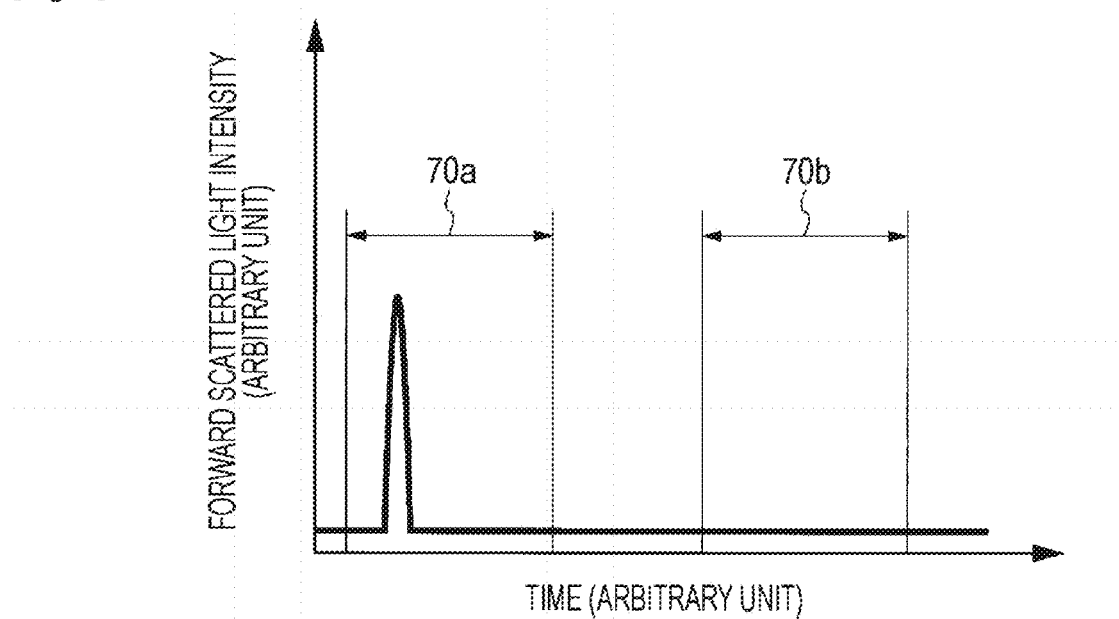
[Fig. 3]
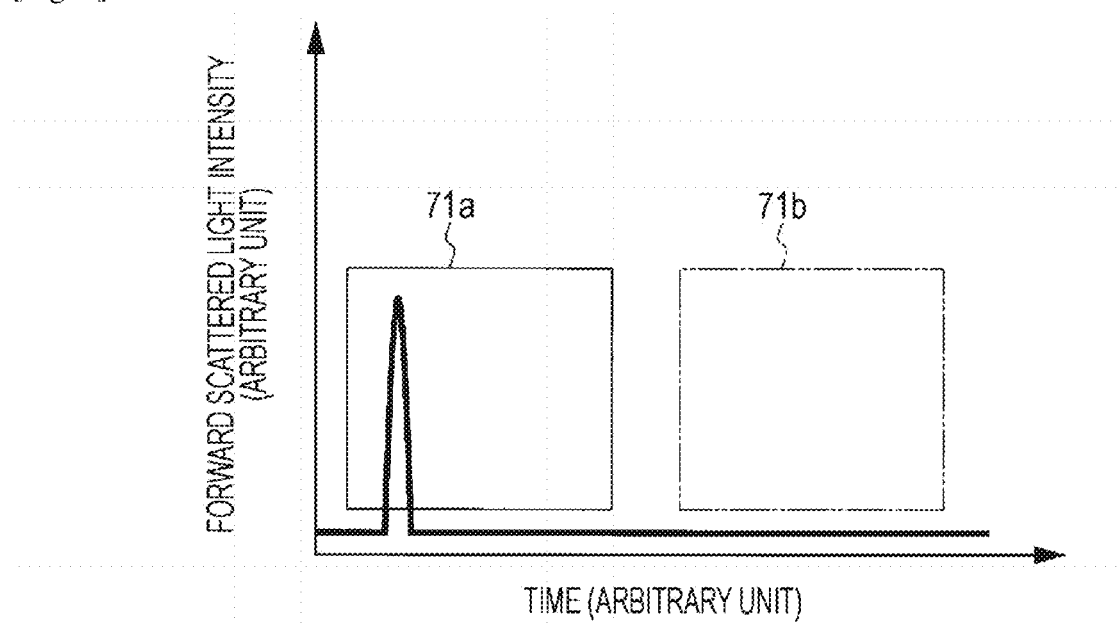

PARTICLE FRACTIONATION APPARATUS, PARTICLE FRACTIONATION METHOD AND PARTICLE FRACTIONATION PROGRAM

CROSS REFERENCE TO RELATED APPLICATIONS

This is a U.S. National Stage Application under 35 U.S.C. §371, based on International Application No. PCT/JP2014/005167, filed Oct. 10, 2014, which claims priority to Japanese Patent Application JP 2013-216633, filed Oct. 17, 2013, each of which is hereby incorporated by reference in its entirety.

This application claims the benefit of Japanese Priority Patent Application JP 2013-216633 filed Oct. 17, 2013, the entire contents of which are incorporated herein by reference.

FIELD

The present disclosure relates to a particle fractionation apparatus, a particle fractionation method, and a particle fractionation program, and more particularly, relates to a technology that sorts and collects particles based on an analysis result according to an optical technique.

BACKGROUND

In related arts, an optical measuring method using a flow cytometry (flow cytometer) is used in analyzing a biological microparticle, such as a cell, a microorganism, or a liposome. The flow cytometer is an analyzing apparatus that irradiates the microparticle, which flows through the inside of a flow path formed of a flow cell or a microchip, with light, and detects fluorescence or scattered light generated from each microparticle.

The flow cytometer includes a function which sorts and collects only the microparticles having specific characteristics, based on an analysis result. Particularly, a microparticle apparatus which considers a cell as a fractionation target is referred to as a 'cell sorter.' In general, the cell sorter makes liquid discharged from the flow path into liquid droplets by applying oscillation to the flow cell or the microchip by an oscillation element or the like (refer to Japanese Unexamined Patent Application Publication No. 2007-532874 and Japanese Unexamined Patent Application Publication No. 2010-190680, which are incorporated herein by reference). After a positive charge or a negative charge is imparted, a progress direction of the liquid droplets separated from the flow path is changed by a deflecting plate or the like, and the liquid droplets are collected by a predetermined container or the like. In addition, in related arts, a technology is suggested which distributes certain cells one by one to each reaction part of a base material used in a polymerase chain reaction (PCR) method or the like, by using a fractionation function by the cell sorter (refer to Japanese Unexamined Patent Application Publication No. 2010-510782, which is incorporated herein by reference).

SUMMARY

When certain particles are distributed to each reaction part of a collecting container or a base material by using the above-described particle fractionation apparatus in the related arts, there is a problem that other particles or foreign substances are mixed in and purity deteriorates. For this reason, a particle fractionation apparatus which can fractionate certain particles at high purity is asked for.

Here, in this disclosure, it is desirable to provide a particle fractionation apparatus which can improve fractionation purity of target particles, a particle fractionation method, and a particle fractionation program.

A particle fractionation apparatus according to the present disclosure includes a charging portion which imparts an electric charge to at least one part of liquid droplets ejected from an orifice that generates a fluid stream, and a first electric charge control portion which controls the charging portion to impart the electric charge to particle non-containing liquid droplets.

When a scattered light detection portion which communicates with the orifice, irradiates a flow path through which at least sheath liquid flows with light, and detects scattered light generated by the irradiation is provided, based on a detection result in the scattered light detection portion, the first electric charge control portion can determine whether or not particles are included in the liquid droplets.

In this case, the scattered light is, for example, forward scattered light.

In addition, when intensity of the scattered light is equal to or less than a threshold value set in advance, the first electric charge control portion can control the charging portion to impart the electric charge to the liquid droplets.

In a certain area and/or at a certain time, when the scattered light is not detected, the first electric charge control portion may control the charging portion to impart the electric charge to the liquid droplets.

Furthermore, the particle fractionation apparatus according to the disclosure may include a second electric charge control portion which controls the charging portion to impart the electric charge to particle containing liquid droplets. In this case, it is possible to arbitrarily select a control by the first electric charge control portion and a control by the second electric charge control portion.

A particle fractionation method according to the disclosure includes imparting an electric charge selectively to particle non-containing liquid droplets among liquid droplets ejected from an orifice which generates a fluid stream.

The particle fractionation method according to the disclosure may further include imparting the electric charge selectively to the particle containing liquid droplets among the liquid droplets ejected from the orifice which generates the fluid stream.

In this case, imparting the electric charge to the particle containing liquid droplets may be performed after imparting the electric charge to the particle non-containing liquid droplets.

It is possible to perform the imparting of the electric charge to the particle non-containing liquid droplets and the imparting of the electric charge to the particle containing liquid droplets, by arbitrary selection.

A program according to the disclosure causes an electric charge control portion of a particle fractionation apparatus to execute a function that imparts the electric charge selectively to the particle non-containing liquid droplets among the liquid droplets ejected from the orifice which generates the fluid stream.

According to some embodiments, a particle fractionating apparatus may comprise a charging portion configured to apply voltages to an electrode that is arranged to contact liquid in a flow path for the liquid, a particle detection system configured to detect when no particle will be contained in a droplet produced from the liquid, and a charge controller connected to the charging portion and configured in a first mode to cause the charging portion to apply charge to the liquid so that the droplet that does not contain a particle will be charged.

In some aspects, a particle fractionating apparatus may further comprise deflecting plates configured to support an electric field between the deflecting plates, such that charged droplets that do not contain particles will be deflected by the deflecting plates. In some implementations, a particle fractionating apparatus may further comprise deflecting plates configured to support an electric field between the deflecting plates, and wherein the charge controller is further operable in a second mode to cause the charging portion to apply charges to droplets produced from the flow path that contain particles such that the charged droplets that contain particles will be deflected by the deflecting plates. In some implementations, a particle fractionating apparatus may further comprise a microchip that includes the flow path and an orifice arranged at an end of the flow path and configured to emit droplets toward the deflecting plates.

According to some aspects, a particle fractionating apparatus may be configured to be manually switched between the first mode and the second mode. In some implementations, the particle detection system comprises a light detector arranged to detect light scattered from the flow path, wherein a signal from the light detector less than a predetermined threshold value indicates the absence of particles. In some aspects, the charge controller is configured in the first mode of operation to apply the voltages to the electrode responsive to at least receiving the signal from the particle detection system within a predetermined time interval.

The foregoing aspects and implementations of features and elements of a particle fractionating apparatus may be used in any suitable combination in an embodiment of a particle fractionating apparatus.

In some embodiments, a method for fractionating particles may comprise acts of determining, by a particle detection system, the absence of particles in droplets produced by the particle fractionating apparatus, and causing, by a charge controller in a first mode of operation, the application of voltages to an electrode arranged to charge the droplets produced by the particle fractionating apparatus that do not contain particles such that the charged droplets that do not contain particles will be charged.

In some implementations, a method may further comprise causing, by the charge controller in a second mode of operation, the application of voltages to the electrode such that droplets that contain particles will be charged. According to some aspects, a method may further comprise receiving, by the charge controller, a signal from a particle detection system that indicates the presence or absence of a particle in a droplet produced by the particle fractionating apparatus. In some implementations, a method may further comprise providing the signal from a scattered light detector that is arranged to detect scattered light from a flow path that is used to form the droplet.

The foregoing aspects and implementations of acts may be used in any suitable combination in an embodiment of a method for fractionating particles.

According to some embodiments, methods of fractionating particles may be implemented as a storage device containing machine-readable instructions that, when executed by a particle fractionating apparatus, cause the particle fractionating apparatus to determine, by a particle detection system, the absence of particles in droplets produced by the particle fractionating apparatus, and cause, by the charge controller in a first mode of operation, the application of charges to the droplets produced by the particle fractionating apparatus that do not contain particles such that the charged droplets that do not contain particles will be charged.

In some implementations, the storage device may further comprise machine-readable instructions that cause the particle fractionating apparatus to cause, by the charge controller in a second mode of operation, the application of charges to droplets produced by the particle fractionating apparatus that contain particles such that the charged droplets that contain particles will be deflected by deflecting plates. In some aspects, instructions for determining the presence or absence of particles in droplets depend upon receiving a signal within a predetermined time interval from a particle detection system, wherein the signal indicates the presence or absence of a particle in a flow path from which the droplets are produced.

The foregoing aspects and implementations of machine-readable instructions may be included in any suitable combination on a storage device.

In some embodiments, a particle fractionating apparatus comprises a scattered light detection system configured to detect when no particle will be contained in a droplet produced from a liquid in a flow path based upon comparing a detected signal with a threshold value, a charging portion configured to apply voltages to an electrode that is arranged to contact the liquid in the flow path, and a charge controller connected to the charging portion and operable in a first mode to cause the charging portion to apply a plurality of different voltages to the electrode responsive to receiving detected signals from the scattered light detection system that indicate no particles will be contained in droplets produced from the liquid.

In some implementations, the particle fractionating apparatus may further comprise deflecting plates, wherein the applied plurality of different voltages are selected to charge the droplets so that they will be deflected to a plurality of predetermined locations by the deflecting plates. According to some aspects, the particle fractionating apparatus may further comprise an orifice arranged at an end of the flow path, wherein the orifice and flow path are disposed on a microfluidic chip. In some aspects, the particle fractionating apparatus is configured to be manually switched between the first mode and a second mode of operation. In some implementations, the charge controller is configured to cause the charging portion to apply the plurality of different voltages only when the detected signals are received within predetermined time intervals. According to some aspects, the scattered light detection system comprises a detector arranged to detect forward scattered light, sideward scattered light, Rayleigh scattered light, or Mie scattered light.

The foregoing aspects and implementations of elements and features of a particle fractionating apparatus may be used in any suitable combination in an embodiment of a particle fractionating apparatus.

According to the disclosure, it is possible to prevent other particles or foreign substances from being mixed in, and to fractionate target particles at high purity. Effects described here are not necessarily limited, and may be any effects described in the disclosure.

BRIEF DESCRIPTION OF DRAWINGS

The skilled artisan will understand that the figures, described herein, are for illustration purposes only. It is to be understood that in some instances various aspects may be shown exaggerated or enlarged to facilitate an understanding of the embodiments. The drawings are not necessarily to scale, emphasis instead being placed upon illustrating the principles of the teachings. The drawings are not intended to limit the scope of the present teachings in any way.

FIG. 1 is a schematic view showing a configuration example of a particle fractionation apparatus according to an embodiment of the disclosure.

FIG. 2 is a view showing a technique for determining 'particle containing' or 'particle non-containing' when a horizontal axis represents time and a vertical axis represents forward scattered light intensity.

FIG. 3 is a view showing a technique for determining 'particle containing' or 'particle non-containing' when a horizontal axis represents time and a vertical axis represents forward scattered light intensity.

The features and advantages of the embodiments will become more apparent from the detailed description set forth below when taken in conjunction with the drawings.

DESCRIPTION OF EMBODIMENTS

Hereinafter, an embodiment according to the disclosure will be described in detail with reference to the attached drawings. The disclosure is not limited to each embodiment described below.

1-1. Overall Configuration of Apparatus

FIG. 1 is a schematic view showing a configuration example of a particle fractionation apparatus according to an embodiment of the disclosure. A particle fractionation apparatus 1 according to the embodiment sorts and collects particles based on an analysis result by an optical technique or the like. As shown in FIG. 1, the particle fractionation apparatus 1 includes a microchip 2, an oscillation element 3, a charging portion 4, an electric charge control portion 7, and deflecting plates 5a and 5b.

1-2. Particles

Particles which are analyzed and fractionated by the particle fractionation apparatus 1 of the embodiment include biological microparticles such as a cell, a microorganism, or a liposome, or synthetic particles such as latex particles, gel particles, or industrial particles.

The biological microparticles include a chromosome, a liposome, a mitochondria, or an organelle which compose various cells. In addition, the cell includes a plant cell, an animal cell, or a blood cell. Furthermore, the microorganism includes a bacteria such as a coliform bacillus, a virus such as a tobacco mosaic virus, or a fungus such as a yeast fungus. The biological microparticles can even include a biological polymer, such as a nucleic acid, a protein, or a complex thereof.

Meanwhile, examples of the industrial particles can include particles formed by an organic polymeric material, an inorganic material, or a metal material. As the organic polymeric material, it is possible to use polystyrene, styrene-divinyl benzene, or polymethyl methacrylate. In addition, as the inorganic material, it is possible to use glass, silica, or a magnetic material. As the metal material, it is possible to use a gold colloid or aluminum. In addition, shapes of these particles are generally spherical, but may be non-spherical. A size or a weight is also not particularly limited.

1-3. Microchip

In the microchip 2, a sample inlet 22 to which the liquid (sample liquid) including particles as a fractionation target is introduced, a sheath inlet 23 to which the sheath liquid is introduced, and an absorption outlet 24 for eliminating a blockage or air bubbles, are formed. In the microchip 2, the sample liquid is introduced into the sample inlet 22, is merged with the sheath liquid introduced into the sheath inlet 23, sends the liquid to a sample flow path, and ejects the liquid from an orifice 21 provided at an end edge of the sample flow path.

In addition, an absorption flow path which communicates with the absorption outlet 24 is connected to the sample flow path. When the blockage or the air bubbles are generated in the sample flow path, the absorption flow path temporarily backflows a flow by making the inside of the sample flow path have a negative pressure and eliminates the blockage or the air bubbles. A negative pressure source, such as a vacuum pump, is connected to the absorption outlet 24.

The microchip 2 can be formed by glass or various types of plastics (PP, PC, COP, PDMS, or the like). It is preferable that material of the microchip 2 be a material which has few optical errors since the material has transmissivity with respect to measurement light irradiated from a light detection portion which will be described later, has low intrinsic fluorescence, and has low wavelength dispersion.

Molding the microchip 2 can be performed by wet etching or dry etching of a glass-made substrate, by nanoimprint or injection molding of a plastic-made substrate, and by machining. The microchip 2 can be formed by sealing a substrate which molds the sample flow path or the like onto a substrate which is made of the same or different material.

1-4. Oscillation Element

The oscillation element 3 is disposed to abut against a part of the microchip 2 or is provided as an internal configuration of the microchip 2. The oscillation element 3 imparts minute oscillation to the sheath liquid by oscillating the microchip 2 at a predetermined frequency, makes the liquid (the sample liquid and the sheath liquid) ejected from the orifice 21 into the liquid droplets, and generates a fluid stream (flow of the liquid droplets) S. As the oscillation element 3, it is possible to use a piezoelectric element or the like.

1-5. Charging Portion

The charging portion 4 imparts the positive or negative electric charge to the liquid droplets ejected from the orifice 21, and is configured to have a voltage source (voltage supply portion 42) which applies a predetermined voltage to an electric charge electrode 41 and the electrode 41. The electric charge electrode 41 is disposed to be in contact with the sheath liquid and/or the sample liquid which flows through the flow path, and imparts the electric charge to the sheath liquid and/or the sample liquid, and is inserted into an electric charge electrode inlet of the microchip 2, for example.

In addition, in FIG. 1, the electric charge electrode 41 is disposed to be in contact with the sample liquid, but the disclosure is not limited thereto. The electric charge electrode 41 may be disposed to be in contact with the sheath liquid, and may be in contact with both of the sample liquid and the sheath liquid. However, considering an influence on the cell of the fractionation target, it is preferable that the electric charge electrode 41 be disposed to be in contact with the sheath liquid.

In this manner, by imparting the positive and negative electric charge to predetermined liquid droplets, it is possible to separate arbitrary liquid droplets by an electrical force. In addition, by synchronizing an electric charge timing by the charging portion 4 and voltage supplied to the oscillation element 3, it is possible to impart the electric charge only to the arbitrary liquid droplets.

1-6. Deflecting Plates

By the electrical force which operates between the electric charges imparted to the liquid droplets, the deflecting plates 5a and 5b change a progress direction of each liquid droplet in the fluid stream S, induce predetermined collecting containers 6a and 6b, and are disposed to interpose the fluid stream S and to face each other. In the deflecting plates 5a and 5b, it is possible to use the electrode which is generally used.

When the positive or negative voltage is applied to the deflecting plates 5a and 5b, respectively, and when the liquid droplets which are electrically charged flow through an electric field formed by applying the voltage, the electrical force (Coulomb force) is generated, and each liquid droplet is gravitated to any one of directions of the deflecting plates 5a and 5b. In the particle fractionation apparatus 1, by changing the positive and negative electric charge and an amount of the electric charge to the liquid droplets, it is possible to control a direction of the flow (side stream) of the liquid droplets gravitated by the electric field. For this reason, it is possible to simultaneously fractionate a plurality of particles which are different from each other. In addition, it is possible to perform the fractionation of the particle containing liquid droplets and the fractionation of the particle non-containing liquid droplets simultaneously or sequentially.

1-7. Collecting Containers

The collecting containers 6a and 6b collect the liquid droplets which flow between the deflecting plates 5a and 5b, and can use a base material in which a general-purpose plastic-made tube, a glass tube, or a plurality of reaction parts (well) are formed for an experiment. It is preferable that the collecting containers 6a and 6b be disposed to be exchangeable in the apparatus.

For example, as shown in FIG. 1, when the collecting container 6a in a tube shape and the collecting container 6b (substrate) provided with a plurality of collecting parts (reaction parts) are used, the collecting container 6a receives non-objective particles, and it is possible to distribute certain particles one by one to each collecting part of the collecting container 6b. In this case, a liquid discharge path of the collected liquid may be connected to the collecting container 6a.

In addition, the number or type of the collecting container disposed in the particle fractionation apparatus 1 is not particularly limited. In addition, when 3 or more collecting containers are disposed, each liquid droplet may be induced to any one of the collecting containers according to a presence or absence, and a size of an electrical working force between the deflecting plates 5a and 5b, and be collected.

1-8. Electric Charge Control Portion

The electric charge control portion 7 controls imparting the electric charge to the liquid droplets, and is provided with a first electric charge control portion which carries out 'particle non-containing liquid droplets mode' that controls the charging portion to impart the predetermined electric charge to the particle non-containing liquid droplets. A method for determining 'particle containing' and 'particle non-containing' with respect to each liquid droplet is not particularly limited, but it is possible to determine based on a detection result of the scattered light measured by the light detection portion which will be described later.

In a case of determination based on the detection result of the scattered light, the electric charge control portion 7 determines 'particle non-containing' when intensity of the scattered light is equal to or less than a threshold value set in advance, controls the voltage supply portion 42 to impart the electric charge to the liquid droplets, and applies the voltage to the electric charge electrode 41. At that time, in a certain area and/or at a certain time, it is preferable that the first electric charge control portion determine a case where the scattered light is not detected or a case where the intensity of the scattered light is equal to or less than the threshold value as 'particle non containing', and control the charging portion to impart the electric charge to the liquid droplets. Accordingly, it is possible to collect the liquid droplets which are not mixed with the particles or the foreign substances to each collecting part (reaction part) of the collecting container 6a or the collecting container 6b.

In addition, in the electric charge control portion 7, a second electric charge control portion which carries out the 'particle containing liquid droplets mode' that controls the charging portion to impart the predetermined electric charge to the particle containing liquid droplets may be provided. The 'particle containing liquid droplets mode' is a general particle fractionation mode, determines whether or not a particle is the target to be obtained based on the fluorescence and the scattered light detected by the detection portion which will be described later, controls the voltage supply portion 42 by the second electric charge control portion, and applies the predetermined voltage to the electric charge electrode 41.

In the particle fractionation apparatus 1 of the embodiment, a user may arbitrarily select whether the 'particle non-containing liquid droplets mode' is carried out or the 'particle containing liquid droplets mode' is carried out in the electric charge control portion 7. In addition, the particle fractionation apparatus 1 may also be set in advance to carry out the 'particle containing liquid droplets mode' by the second electric charge control portion after carrying out the 'particle non-containing liquid droplets mode' by the first electric charge control portion.

1-9. Light Detection Portion

Furthermore, in the particle fractionation apparatus 1 of the embodiment, there is provided the light detection portion (not shown) which irradiates a predetermined part of the sample flow path with the light (measurement light) and detects the light (measurement target light) generated from the particles that flow through the sample flow path. The light detection portion can be configured to be similar to a flow cytometry in the related arts. Specifically, the light detection portion is configured to have a laser light source, an irradiation system provided with a condenser which concentrates laser light and irradiates the particles with the laser light, a dichroic mirror, or a band pass filter, and a detection system which detects the measurement target light generated from the particles by irradiation with the later light.

The detection system is configured to have an area imaging element, such as a photo multiplier tube (PMT), a CCD, or a CMOS element. In addition, even though the irradiation system and the detection system are configured to have the same optical path, the irradiation system and the detection system may be configured to have a separate optical path. In addition, the measurement target light detected by the detection system of the light detection portion is the light generated from the particles by irradiation with the measurement light, and for example, can be various types of scattered light or fluorescence, such as forward scattered light, sideward scattered light, Rayleigh scattered light, or Mie scattered light.

Since the intensity of the forward scattered light among the measurement target light changes in proportion to a surface area of the cell, and becomes an index for evaluating the size of the particles, a general particle fractionation apparatus is provided with the detection system. The particle fractionation apparatus 1 of the embodiment determines 'particle containing' or 'particle non-containing' in the above-described electric charge control portion 7, and uses the detection result of the detection system provided for analyzing the particles.

2-1. Operation

Next, an operation of the particle fractionation apparatus 1 of the embodiment, that is, a method for fractionating the particles using the particle fractionation apparatus 1 is described by dividing the case into a case where the 'particle non-containing liquid droplets mode' is selected by the user, and a case where the 'particle containing liquid droplets mode' is selected by the user.

2-2. Particle Non-Containing Liquid Droplets

The 'particle non-containing liquid droplets mode' is a mode for selectively collecting the liquid droplets in which the particles or the foreign substances are not included in a part or an entirety of the reaction part of the collecting container or the base material. In a case where the biological microparticles, such as a certain cell, are separated and collected, the mode is used when a conservation solution for preventing the biological microparticles from being dried is distributed to the reaction part of the collecting container or the base material. Examples of the conservation solution which is used at that time can include a saline solution, and in general the sheath liquid is used.

When the 'particle non-containing liquid droplets mode' is carried out, only the sheath liquid is introduced to and flows through the microchip 2. Based on the result of performing the detection of the scattered light by the light detection portion, it is determined whether the liquid droplets discharged from the orifice 21 are the 'particle containing liquid droplets' or the 'particle non-containing liquid droplets.' A method for determining whether the liquid droplets are the 'particle containing liquid droplets' or the 'particle non-containing liquid droplets' is not particularly limited. However, in a case of determination by the scattered light, it is possible to employ a method in which a case where a signal that exceeds the threshold value is not detected for a certain period of time is 'particle non-containing.'

FIG. 2 and FIG. 3 are views showing a technique for determining 'particle containing' or 'particle non-containing' when a horizontal axis represents time and a vertical axis represents the forward scattered light intensity. When a detection result as shown in FIG. 2 is obtained by the light detection portion, and when the detected intensity of the scattered light exceeds the threshold value set in advance during the determination time period 70a set in advance, the electric charge control portion 7 determines that the particles or the foreign substances are mixed in. Then, the first electric charge control portion of the electric charge control portion 7 controls the voltage supply portion 42 not to impart the electric charge to the liquid droplets that correspond to a detection range, or controls the voltage supply portion 42 to induce the liquid droplets to a disposable container and applies the predetermined voltage to the electric charge electrode 41.

Meanwhile, during a determination time period 70b set in advance, when the detected intensity of the scattered light does not exceed the threshold value set in advance, 'particle non-containing' is determined, the voltage supply portion 42 is controlled by the first electric charge control portion of the electric charge control portion 7, and the predetermined voltage is applied to the electric charge electrode 41. Accordingly, the charged liquid droplets change the progress direction thereof by the deflecting plates 5a and 5b, are induced to each collecting part (reaction part) of the predetermined collecting container 6a or the collecting container 6b, and are collected.

In addition, as shown in FIG. 3, by using an image process, it is confirmed whether there is a peak in the scattered light in the certain area (determination areas 71a and 71b) or not. As a result, it is possible to determine 'particle containing' or 'particle non-containing.' Specifically, a case where there is a peak of the scattered light in the determination area 71a set in advance is determined as 'particle containing'. A case where there is not a peak of the scattered light in the determination area 71b is determined as 'particle non-containing'. Based on the determination result, the first electric charge control portion of the electric charge control portion 7 controls the charging portion 4.

Meanwhile, based on the detection result of the light detection portion, the 'particle containing liquid droplets mode' is a general particle fractionation mode in which the certain particles are separated and collected. When the 'particle containing liquid droplets mode' is carried out by the particle fractionation apparatus 1 of the embodiment, the sample liquid including the target particles to be fractionated in the sample inlet 22 and the sheath liquid in the sheath inlet 23 are introduced, respectively. In a laminar flow of the sample liquid and the sheath liquid, in the light detection portion, optical characteristics of the particles are detected, and at the same time, a speed of the flow (flow speed) of the particles or an interval between the particles is detected.

The detected optical characteristics, the flow speed, or the interval of the particles is converted into the electrical signal and is output to the entire control portion (not shown) of the apparatus. In the entire control portion, it is determined whether there is the target particle to be obtained or not based on the fluorescence or the scattered light detected by the light detection portion. Based on the determination result, the second electric charge control portion controls the voltage supply portion 42, and applies the predetermined voltage to the electric charge electrode 41.

After that, the laminar flow of the sample liquid and the sheath liquid are discharged to a space out of the microchip 2 from the orifice 21. At that time, the oscillation element 3 oscillates the orifice 21 and makes the discharged liquid into the liquid droplets. At that time, each charged liquid droplet changes the progress direction thereof by the deflecting plates 5a and 5b, is induced to the predetermined collecting container or reaction part, and is collected.

The user can arbitrarily select the above-described 'particle non-containing liquid droplets mode' or 'particle containing liquid droplets mode'. However, the 'particle containing liquid droplets mode' may be set in advance to be carried out after the 'particle non-containing liquid droplets mode' is carried out. The 'particle non-containing liquid droplets mode' and the 'particle containing liquid droplets mode' may be set to be carried out alternately.

The above-described 'particle non-containing liquid droplets mode' may create a program for realizing a function of imparting the electric charge selectively to the particle non-containing liquid droplets among the liquid droplets discharged from the orifice, mount the program on the electric charge control portion 7, and implement the program to the particle fractionation apparatus 1. In addition, in the electric charge control portion 7 of the particle fractionation apparatus 1, it is possible to mount the program for realizing the 'particle containing liquid droplets mode' together with the 'particle non-containing liquid droplets mode' program.

In addition, in the above-described first embodiment, a case where the microchip 2 is used is described as an example, but the disclosure is not limited thereto. The similar effect can be obtained by using a flow cell instead of the microchip 2.

As described above, in the particle fractionation apparatus of the embodiment, there is provided a first electric charge control portion which carries out the 'particle non-containing liquid droplets mode' that controls the charging portion to impart the electric charge to the particle non-containing liquid droplets. When the 'particle non-containing liquid droplets mode' is performed, it is possible to distribute only the liquid droplets in which the particles or the foreign substances are not mixed in to the reaction part of the collecting container or the base material. After that, by fractionating the particles by the 'particle containing liquid droplets mode', for example, it is possible to fractionate the target particles at high purity. As a result, it is possible to further improve the fractionation purity than the particle fractionation apparatus in the related arts.

In addition, the disclosure can have a configuration as described below.

(1)

A particle fractionation apparatus which includes: a charging portion which imparts an electric charge to at least one part of liquid droplets ejected from an orifice that generates a fluid stream; and a first electric charge control portion which controls the charging portion to impart the electric charge to particle non-containing liquid droplets.

(2)

The particle fractionation apparatus described in (1), in which a scattered light detection portion which communicates with the orifice, irradiates a flow path through which at least a sheath liquid flows with light, and detects scattered light generated by the irradiation is provided. Based on a detection result in the scattered light detection portion, the first electric charge control portion determines whether or not particles are included in the liquid droplets.

(3)

The particle fractionation apparatus described in (2), in which the scattered light is forward scattered light.

(4)

The particle fractionation apparatus described in (2) or (3), in which, when intensity of the scattered light is equal to or less than a threshold value set in advance, the first electric charge control portion controls the charging portion to impart the electric charge to the liquid droplets.

(5)

The particle fractionation apparatus described in any one of (2) to (4), in which, in a certain area and/or at a certain time, when the scattered light is not detected, the first electric charge control portion controls the charging portion to impart the electric charge to the liquid droplets.

(6)

The particle fractionation apparatus described in any one of (1) to (5), which, further includes a second electric charge control portion which controls the charging portion to impart the electric charge to particle containing liquid droplets, and can arbitrarily select a control by the first electric charge control portion and a control by the second electric charge control portion.

(7)

A particle fractionation method which includes imparting an electric charge selectively to particle non-containing liquid droplets among liquid droplets ejected from an orifice which generates a fluid stream.

(8)

The particle fractionation method described in (7), which includes imparting the electric charge selectively to the particle containing liquid droplets among the liquid droplets ejected from the orifice which generates the fluid stream.

(9)

The particle fractionation method described in (8), in which imparting the electric charge to the particle containing liquid droplets is performed after the imparting of the electric charge to the particle non-containing liquid droplets.

(10)

The particle fractionation method described in (8), in which the imparting of the electric charge to the particle non-containing liquid droplets and the imparting of the electric charge to the particle containing liquid droplets are performed by arbitrary selection.

(11)

A program which causes an electric charge control portion of a particle fractionation apparatus to execute a function that imparts the electric charge selectively to the particle non-containing liquid droplets among the liquid droplets ejected from the orifice which generates the fluid stream.

(12)

A particle fractionating apparatus comprising: a charging portion configured to apply voltages to an electrode that is arranged to contact liquid in a flow path for the liquid; a particle detection system configured to detect when no particle will be contained in a droplet produced from the liquid; and a charge controller connected to the charging portion and configured in a first mode to cause the charging portion to apply charge to the liquid so that the droplet that does not contain a particle will be charged.

(13)

The particle fractionating apparatus of (12), further comprising deflecting plates configured to support an electric field between the deflecting plates such that charged droplets that do not contain particles will be deflected by the deflecting plates.

(14)

The particle fractionating apparatus of (12), further comprising deflecting plates configured to support an electric field between the deflecting plates and wherein the charge controller is further operable in a second mode to cause the charging portion to apply charges to droplets produced from the flow path that contain particles such that the charged droplets that contain particles will be deflected by the deflecting plates.

(15)

The particle fractionating apparatus of (14), wherein the particle fractionating apparatus is configured to be manually switched between the first mode and the second mode.

(16)

The particle fractionating apparatus of (12), where the particle detection system comprises a light detector arranged to detect light scattered from the flow path, wherein a signal from the light detector less than a predetermined threshold value indicates the absence of particles.

(17)

The particle fractionating apparatus of (16), wherein the charge controller is configured in the first mode of operation to apply the voltages to the electrode responsive to at least receiving the signal from the particle detection system within a predetermined time interval.

(18)

The particle fractionating apparatus of (12), further comprising a microchip that includes the flow path and an orifice arranged at an end of the flow path and configured to emit droplets toward the deflecting plates.

(19)
A method for fractionating particles, the method comprising: determining, by a particle detection system, the absence of particles in droplets produced by the particle fractionating apparatus; and causing, by a charge controller in a first mode of operation, the application of voltages to an electrode arranged to charge the droplets produced by the particle fractionating apparatus that do not contain particles such that the charged droplets that do not contain particles will be charged.

(20)
The method of (19), further comprising: causing, by the charge controller in a second mode of operation, the application of voltages to the electrode such that droplets that contain particles will be charged.

(21)
The method of (19), further comprising receiving, by the charge controller, a signal from a particle detection system that indicates the presence or absence of a particle in a droplet produced by the particle fractionating apparatus.

(22)
The method of (21), further comprising providing the signal from a scattered light detector that is arranged to detect scattered light from a flow path that is used to form the droplet.

(23)
A storage device containing machine-readable instructions that, when executed by a particle fractionating apparatus, cause the particle fractionating apparatus to: determine, by a particle detection system, the absence of particles in droplets produced by the particle fractionating apparatus; and cause, by the charge controller in a first mode of operation, the application of charges to the droplets produced by the particle fractionating apparatus that do not contain particles such that the charged droplets that do not contain particles will be charged.

(24)
The storage device of (23), further comprising machine-readable instructions that, when executed by the particle fractionating apparatus, cause the particle fractionating apparatus to cause, by the charge controller in a second mode of operation, the application of charges to droplets produced by the particle fractionating apparatus that contain particles such that the charged droplets that contain particles will be deflected by deflecting plates.

(25)
The storage device of (24), wherein instructions for determining the presence or absence of particles in droplets depend upon receiving a signal within a predetermined time interval from a particle detection system, wherein the signal indicates the presence or absence of a particle in a flow path from which the droplets are produced.

(26)
A particle fractionating apparatus comprising: a scattered light detection system configured to detect when no particle will be contained in a droplet produced from a liquid in a flow path based upon comparing a detected signal with a threshold value; a charging portion configured to apply voltages to an electrode that is arranged to contact the liquid in the flow path; and a charge controller connected to the charging portion and operable in a first mode to cause the charging portion to apply a plurality of different voltages to the electrode responsive to receiving detected signals from the scattered light detection system that indicate no particles will be contained in droplets produced from the liquid.

(27)
The particle fractionating apparatus of (26), further comprising deflecting plates, wherein the applied plurality of different voltages are selected to charge the droplets so that they will be deflected to a plurality of predetermined locations by the deflecting plates.

(28)
The particle fractionating apparatus of (26), wherein the particle fractionating apparatus is configured to be manually switched between the first mode and a second mode of operation.

(29)
The particle fractionating apparatus of (26), wherein the charge controller is configured to cause the charging portion to apply the plurality of different voltages only when the detected signals are received within predetermined time intervals.

(30)
The particle fractionating apparatus of (26), further comprising an orifice arranged at an end of the flow path, wherein the orifice and flow path are disposed on a microfluidic chip.

(31)
The particle fractionating apparatus of (26), wherein the scattered light detection system comprises a detector arranged to detect forward scattered light, sideward scattered light, Rayleigh scattered light, or Mie scattered light.

REFERENCE SIGNS LIST

1 Particle fractionation apparatus
2 Microchip
3 Oscillation element
4 Charging portion
5a, 5b Deflecting plate
6a, 6b Collecting container
7 Electric charge control portion
21 Orifice
22 Sample inlet
23 Sheath inlet
24 Absorption outlet
41 Electrode
42 Voltage supply portion
70a, 70b Determination time
71a, 71b Determination area
S Fluid stream It should be understood by those skilled in the art that various modifications, combinations, sub-combinations and alterations may occur depending on design requirements and other factors insofar as they are within the scope of the appended claims or the equivalents thereof.

The invention claimed is:
1. A particle fractionating apparatus comprising:
a charging portion configured to apply plural sorting voltages to an electrode that is arranged to contact liquid in a flow path for the liquid;
a particle detection system configured to detect when no particle will be contained in a droplet produced from the liquid; and
a charge controller connected to the charging portion and configured in a first mode to cause the charging portion, in response to signals from the particle detection system, to apply a first sorting voltage to the electrode to charge the liquid so that a first droplet that does not contain a particle will be charged to a first amount and to apply a second sorting voltage to the electrode to charge the liquid so that a second droplet that does not contain a particle will be charged to a second amount different from the first amount.

2. The particle fractionating apparatus of claim 1, further comprising deflecting plates configured to support an electric field between the deflecting plates such that charged droplets that do not contain particles will be deflected by the deflecting plates.

3. The particle fractionating apparatus of claim 1, further comprising deflecting plates configured to support an electric field between the deflecting plates and wherein the charge controller is further operable in a second mode to cause the charging portion to apply charges to droplets produced from the flow path that contain particles such that the charged droplets that contain particles will be deflected by the deflecting plates.

4. The particle fractionating apparatus of claim 3, wherein the particle fractionating apparatus is configured to be manually switched between the first mode and the second mode.

5. The particle fractionating apparatus of claim 1, where the particle detection system comprises a light detector arranged to detect light scattered from the flow path, wherein a signal from the light detector less than a predetermined threshold value indicates the absence of particles.

6. The particle fractionating apparatus of claim 5, wherein the charge controller is configured in the first mode of operation to apply the first sorting voltage to the electrode responsive to at least receiving the signal from the particle detection system within a predetermined time interval.

7. The particle fractionating apparatus of claim 1, further comprising a microchip that includes the flow path and an orifice arranged at an end of the flow path and configured to emit droplets toward the deflecting plates.

8. A method for fractionating particles, the method comprising:
 determining, by a particle detection system, an absence of particles in a first droplet produced by the particle fractionating apparatus;
 causing, by a charge controller in a first mode of operation, application of a first sorting voltage to an electrode arranged to charge the first droplet such that the first droplet that does not contain particles will be charged to a first amount;
 determining, by the particle detection system, an absence of particles in a second droplet produced by the particle fractionating apparatus; and
 causing, by the charge controller in the first mode of operation, application of a second sorting voltage to the electrode such that the second droplet that does not contain particles will be charged to a second amount different from the first amount.

9. The method of claim 8, further comprising:
 causing, by the charge controller in a second mode of operation, application of voltages to the electrode such that droplets that contain particles will be charged.

10. The method of claim 8, further comprising receiving, by the charge controller, a signal from a particle detection system that indicates presence or absence of a particle in a droplet produced by the particle fractionating apparatus.

11. The method of claim 10, further comprising providing a signal from a scattered light detector that is arranged to detect scattered light from a flow path that is used to form the droplet.

12. A storage device containing machine-readable instructions that, when executed by a particle fractionating apparatus, cause the particle fractionating apparatus to:
 determine, by a particle detection system, an absence of particles in a first droplet produced by the particle fractionating apparatus;
 cause, by a charge controller in a first mode of operation, application of a first charge to the first droplet such that the first droplet that does not contain particles will be charged to a first amount;
 determine, by the particle detection system, an absence of particles in a second droplet produced by the particle fractionating apparatus; and
 cause, by the charge controller in the first mode of operation, application of a second charge to the second droplet such that the second droplet that does not contain particles will be charged to a second amount different from the first amount.

13. The storage device of claim 12, further comprising machine-readable instructions that, when executed by the particle fractionating apparatus, cause the particle fractionating apparatus to cause, by the charge controller in a second mode of operation, application of charges to droplets produced by the particle fractionating apparatus that contain particles such that the charged droplets that contain particles will be deflected by deflecting plates.

14. The storage device of claim 13, wherein instructions for determining a presence or absence of particles in droplets depend upon receiving a signal within a predetermined time interval from the particle detection system, wherein the signal indicates the presence or absence of a particle in a flow path from which the droplets are produced.

15. A particle fractionating apparatus comprising:
 a scattered light detection system including a light detector and processing electronics configured to detect a signal indicating an amount of light passing through a droplet produced from a liquid in a flow path and determine when no particle will be contained in the droplet based upon comparing the detected signal with a threshold value;
 a charging portion configured to apply voltages to an electrode that is arranged to contact the liquid in the flow path;
 a charge controller connected to the charging portion and configured to operate in a first mode to cause the charging portion to apply a plurality of different voltages to the electrode responsive to receiving detected signals from the scattered light detection system that indicate no particles will be contained in droplets produced from the liquid;
 and deflecting plates, wherein the applied plurality of different voltages are selected to charge the droplets so that they will be deflected to a plurality of predetermined locations by the deflecting plates.

16. The particle fractionating apparatus of claim 15, wherein the particle fractionating apparatus is configured to be manually switched between the first mode and a second mode of operation.

17. The particle fractionating apparatus of claim 15, wherein the charge controller is configured to cause the charging portion to apply the plurality of different voltages only when the detected signals are received within predetermined time intervals.

18. The particle fractionating apparatus of claim 15, further comprising an orifice arranged at an end of the flow path, wherein the orifice and flow path are disposed on a microfluidic chip.

19. The particle fractionating apparatus of claim 15, wherein the scattered light detection system comprises a detector arranged to detect forward scattered light, sideward scattered light, Rayleigh scattered light, or Mie scattered light.

* * * * *